United States Patent
Schliesser et al.

(10) Patent No.: US 8,674,325 B2
(45) Date of Patent: Mar. 18, 2014

(54) METHOD AND DEVICE FOR THE QUANTITATIVE REAL TIME ANALYSIS OF FLUORESCENT SAMPLES

(75) Inventors: Rainer Schliesser, Stuhr (DE); Norbert Wittschief, Achim (DE); Rainer Treptow, Norderstedt (DE); Gerd Joachim Eckert, Hamburg (DE); Andreas Schirr, Hamburg (DE)

(73) Assignee: Eppendorf AG, Hamburg (DE)

( * ) Notice: Subject to any disclaimer, the term of this patent is extended or adjusted under 35 U.S.C. 154(b) by 743 days.

(21) Appl. No.: 12/445,267

(22) PCT Filed: Oct. 10, 2007

(86) PCT No.: PCT/EP2007/008809
§ 371 (c)(1),
(2), (4) Date: Jun. 25, 2010

(87) PCT Pub. No.: WO2008/043541
PCT Pub. Date: Apr. 17, 2008

(65) Prior Publication Data
US 2010/0285599 A1    Nov. 11, 2010

(30) Foreign Application Priority Data
Oct. 12, 2006  (DE) .......................... 10 2006 048 346

(51) Int. Cl.
*G01J 1/58* (2006.01)
(52) U.S. Cl.
USPC .................................. 250/458.1; 250/459.1
(58) Field of Classification Search
USPC .......................................... 250/458.1, 459.1
See application file for complete search history.

(56) References Cited

U.S. PATENT DOCUMENTS

| 4,300,834 A | 11/1981 | Demers et al. |
| 6,043,880 A * | 3/2000 | Andrews et al. ............... 356/311 |
| 6,197,503 B1 | 3/2001 | Vo-Dinh et al. |
| 6,852,986 B1 | 2/2005 | Lee et al. |

(Continued)

FOREIGN PATENT DOCUMENTS

| EP | 212455 A2 * | 3/1987 |
| EP | 0 241 268 A2 | 4/1987 |

(Continued)

OTHER PUBLICATIONS

Scofield, J.H., "Frequency-domain description of a lock-in amplifier," American Journal of Physics, Amercian Assocation of Physics Teachers, US (62(2):129-133 (1994).

Muschallik, C, et al., "Influence of RF Oscillators on an OFDM Signal," IEEE Transactions on Consumer Electoronics, IEEE Service Center, vol. 41, No. 3: 592-603 (Aug. 1995).

(Continued)

*Primary Examiner* — Christine Sung
(74) *Attorney, Agent, or Firm* — Todd Lorenz; Arnold & Porter LLP

(57) ABSTRACT

A method for the quantitative real time analysis of fluorescent samples is provided, at which each of the samples is excited to fluoresce by a sample individual light source (12) and the intensity of the light which is emitted by the samples is measured. For a highly precise measurement of even low light intensities for the purpose of reduction of the analysis time, each light source (12) is switched on and off-during a defined interval by a clocked pulse sequence of constant pulse frequency alternately. The measurement of the intensity of the emission light during these intervals is exclusively performed during the switch-on phases of the light, source (12).

15 Claims, 2 Drawing Sheets

(56) References Cited

U.S. PATENT DOCUMENTS

Figure 1:
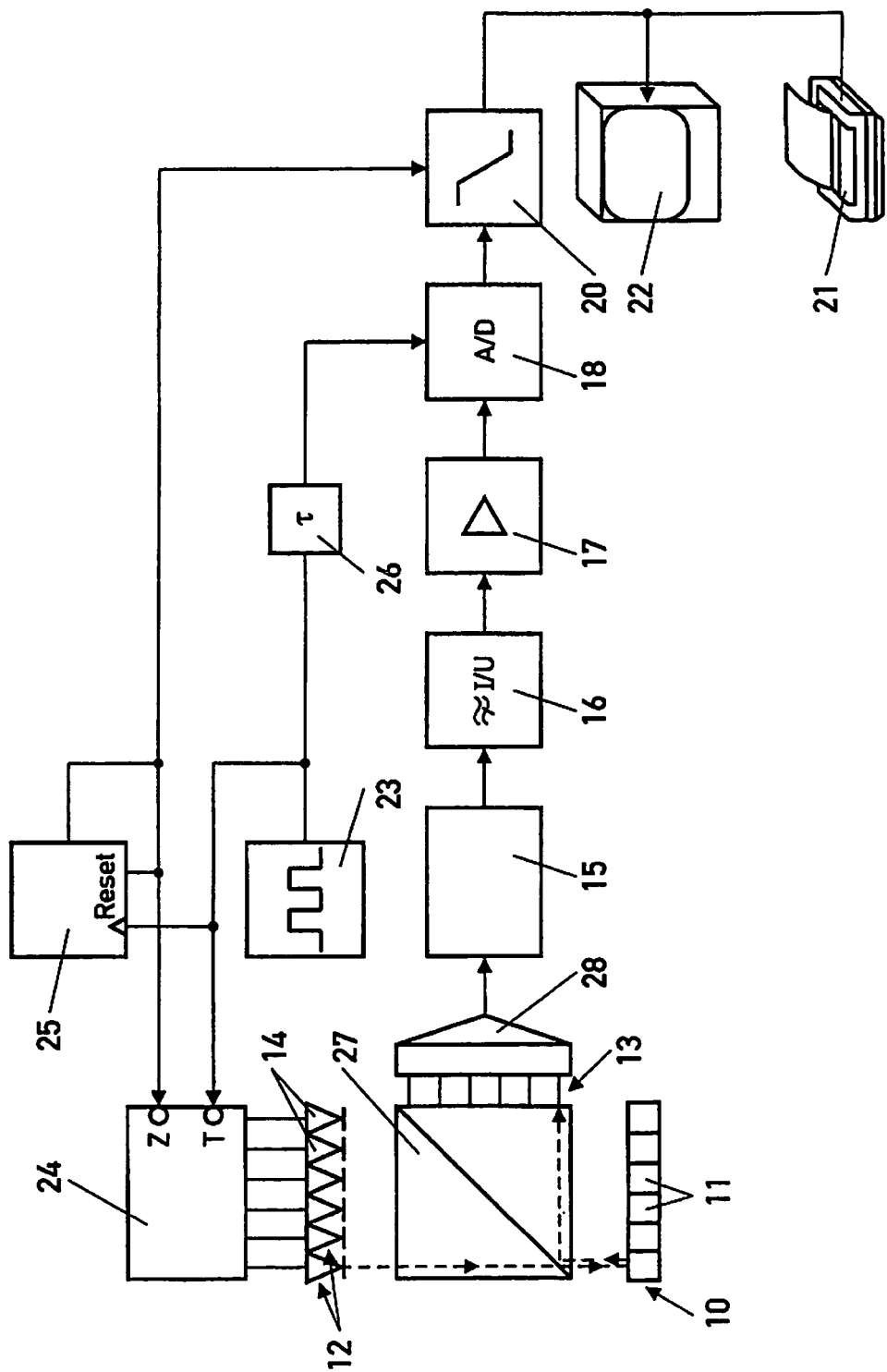

| | | |
|---|---|---|
| 6,870,165 B2 * | 3/2005 | Amirkhanian et al. .... 250/458.1 |
| 6,888,633 B2 | 5/2005 | Vander Jagt et al. |
| 7,102,131 B2 * | 9/2006 | Spolaczyk et al. ....... 250/339.12 |
| 7,148,043 B2 | 12/2006 | Kordunsky et al. |
| 2002/0001080 A1 * | 1/2002 | Miller et al. ................... 356/326 |
| 2003/0016352 A1 * | 1/2003 | Goldman et al. ............. 356/317 |
| 2006/0231745 A1 | 10/2006 | Bodano et al. |
| 2007/0194246 A1 * | 8/2007 | Lee et al. .................... 250/458.1 |
| 2009/0032743 A1 * | 2/2009 | Schirr et al. ............... 250/578.1 |
| 2009/0230323 A1 * | 9/2009 | Lee et al. ................... 250/459.1 |
| 2010/0324834 A1 * | 12/2010 | Treptow et al. ................. 702/32 |

FOREIGN PATENT DOCUMENTS

| | | |
|---|---|---|
| EP | 0902271 A2 | 3/1999 |
| JP | 2005-055622 A | 3/2005 |
| WO | 98-57153 A1 | 12/1998 |
| WO | 01-35079 A1 | 5/2001 |
| WO | 2006/119277 A2 | 5/2006 |

OTHER PUBLICATIONS

Chance, B. et al., "Phase measurement of light absorption and scatter in human tissue," Review of Scientific Instruments, AIP, vol. 69, No. 10: 3457-3481 (Oct. 1998).

* cited by examiner

METHOD AND DEVICE FOR THE QUANTITATIVE REAL TIME ANALYSIS OF FLUORESCENT SAMPLES

CROSS REFERENCE TO RELATED APPLICATIONS

This is the National Stage filed under 35 U.S.C. §371 of International Application PCT/EP2007/008809 filed on Oct. 10, 2007, which designated the United States of America, the disclosure of which is incorporated herein by reference. The present application claims priority from German Patent Application No 10 2006 048 346.4 filed on 12 Oct. 2006, the contents of which are incorporated herein by reference.

The invention relates to a method and device for the quantitative real time analysis of fluorescent samples according to the preamble of claim 1.

Such methods are used amongst others in clinical diagnostics in combination with a polymerase chain reaction, the so called PCR (Polymerase Chain Reaction), for the determination of the amount of DNA (desoxyribonucleic acid). According to a repetitive cycle, a sample of DNA molecules, in order to get copied or amplified respectively, with primers, which serve as start-DNA, and with nucleotides, which are attached to the primers, is heated to 95° C. within a first step of cycle, whereby the complementary strands of the DNA denature. By dropping the temperature to 55° C. within a second step of cycle, hybridization occurs, wherein the primers bind to the DNA. In a third step of cycle the sample is heated to 72° C. At this working temperature, the polymerase do assemble further nucleotides to the growing DNA strands and the loose bonds between primers and those DNA sections, which are not perfectly complementary, break open again. During the permanent repetition of a cycle, which is composed of said three cycle steps, the number of copied DNA molecules is doubled within each new cycle.

In order to determine the DNA molecules formed, the samples are provided with a dye, e.g. ethidium bromide (EtBr), which is fluorescent if it is bound to double stranded DNA-molecules and if excited with light. From the intensity of the light which is emitted by fluorescence, the amount of formed DNA can be derived.

According to a known method of analysis for the analysis of samples (EP 0 902 271 A2), light from a plurality of light sources is guided via a same number of optical fibres to one sample respectively. Light is emitted by each of said samples because of the excitation with light due to fluorescence at consecutive times, which correspond to those times, at which the samples are excited by light sources. For the detection of the amount of light, the so called light intensity, which is emitted by the plurality of samples, a single light detector is used, into which a plurality of optical fibres are conducted, which start from the samples. Hereby, bifurcated optical fibres are used, which provide a trunk with two branches deriving therefrom. Each of said bifurcated optical fibres is assigned to a sample with its trunk, while one fork is assigned to a light source and the other fork is located at the light detector. All of said fork ends, which are located at the light detector, are bundled by a connector (octopus connector). A green filter is positioned between the exit of the connector with its plurality of fork ends and the light detector. LEDs with a wave length from the blue light spectrum are used as light sources. As light detector, preferably a light sensitive amplifier valve, a so called photomultiplier (PM), is used. The photomultiplier generates an electrical signal, which is equivalent to the intensity of the detected light. Said electrical signal is stored in a microcontroller. The light sources are sequentially switched on for a predetermined period respectively and the light intensity of the samples is stored individually until all light sources have been switched-on once. Then, the sequences of measurements are repeated by performing a new sequential activation of all light sources, starting with the first light source. The plurality of measurements for each sample results into a bell-shaped curve, when the measured intensity is plotted against the number of measurements. At 80% of the maximum, from the number of measurements per sample the number of e.g. DNA contained within the sample, is determined.

A known fluorometer for the detection and measurement of light emissions caused by fluorescence (WO 01/35079 A1), which in particular is used in combination with PCR based investigations, has a plurality of light sources, preferably light emitting diodes LEDs, for the illumination of samples which are contained in small containers, has a first optical path between each LED and its assigned container, and a second optical path between each container and optoelectronic means for sensing the optical radiation, which is caused by the samples, if they are excited to fluoresce. As optoelectronic means, a light sensitive amplifier valve, a so called photomultiplier, which generates a charge or signal pulse upon reception of each photon, and a CCD camera are used. By means of said fluorometer, the method for the analysis of PCR-amplified material is performed such that samples, which are to be amplified by PCR, are filled into containers, said samples are illuminated sequentially by said LEDs and the light, which is emitted by the samples due to fluorescence, is detected by said optoelectronic means and the quantity of the light measurement, i.e. the light intensity, is compared with the predetermined reference value.

In order to achieve a reliable result of the analysis, a sufficiently high light intensity is required for the measurement; this is because the measurement of small light intensities is strongly interfered by noise, in particular that of a photomultiplier applied as light detector, by impact sound, capacitive and inductive interferences, supply voltage fluctuations and the like. In order to achieve a sufficiently high light intensity, e.g. for the determination of the amount of DNA, e.g. at a PCR, a plurality of repetitive cycles is required, during which DNA is copied, such that the analysis generally is very time consuming.

It is the object of the invention to improve the method mentioned above, such that already small light intensities can be measured very precise whereby reducing the period for achieving a reliable analysis.

According to the present invention the object is met by the features of claim 1.

The method according to the present invention has the advantage that by the periodical switch-on and switch-off of each light source during a defined time interval and by the measurement of the intensity of the light, which is emitted by the sample during said interval exclusively during the switch-on phase or the activity phase of the light source, those interference signals and occurring noise are not detected, which are occurring during the switch-off phase or the inactivity phase of the light source; this is because all interference quantities, which do not have the same frequency and/or phasing as the clocked pulse sequence, are filtered and do not contribute to the measurement of the light intensity. The higher the number of clocked pulses per period, the better is the achieved filtering of interferences. In consequence, the overall achieved S/N-ratio is already sufficiently good at a low light intensity such that a reliable evaluation of the electrical signal, which represents the light intensity, is possible. Altogether, the period from the start to the point of time, at which a S/N-ratio exists, which allows for a reliable measurement, is extremely shortened by the method according to the present invention and thereby the time period which is required for the method of analysis is strongly reduced.

Appropriate embodiments of the method according to the present invention with advantageous developments and designs according to the present invention arise from the further claims 2 to 9.

According to an advantageous embodiment of the invention, the clocked pulse sequence is generated with a duty cycle of 1:2 and in each of the consecutive time intervals, a couple of light sources is controlled, whereby one light source of the couple of light sources is controlled by the clocked pulse sequence and the other light source is controlled by that clocked pulse sequence, which is shifted by the period of one pulse—and which is therefore inverse to the original clocked pulse sequence. This offers the advantage, that the plurality of existing samples and their assigned light sources are not processed individually and sequentially, but pair-wise, such that the required time of analysis is additionally halved.

According to an advantageous embodiment of the invention, the emission light, which comes from each sample, is converted to an electrical analog signal, which is sampled at time points, which are predetermined by the clocked pulses, und the sampled value is analog/digital converted. All sampled values, which are collected within the interval and digitized, are added und the averaged sum of sampled values is output as a measure for the light intensity. By analog/digital-converting only one sampled value of the analog output signal of the band-pass amplifier and not the complete output signal, only minor demands are made on the ND-converter respective to its dynamics and its noise-insensitivity such that cheaper and slower ND-converter may be accessed. The addition of the sampled values, which have exclusively the same frequency and the same phase, requires only a small hardware effort and is saving computing time, if compared to other evaluation methods, e.g. correlation- or frequency analysis methods.

According to an advantageous embodiment of the invention, the sampling of the analog signal is performed about in the centre of the pulse period of each clocked pulse, preferably shifted from the centre towards the end of the pulse period. This offers the advantage that the sampling is performed within a signal range of the analog signal, in which the analog signal has reached its tuned state, and that therefore the tuning procedure of the analog signal, which is generated by the conversion of the emission light into an electrical signal, is suppressed, in particular in the case if the known light-sensitive amplifier valves or multiplexer with downstream arranged current/voltage converter and band-pass amplifier are used.

According to an advantageous embodiment of the invention, the analog signal is high-pass filtered, current/voltage-converted and amplified band-limited. This offers the advantage that in particular low-frequent interferences like impact sound, capacitive and inductive interferences, power supply interferences and the like, as well as low-frequent noise are eliminated and only an analog signal, which lies within the pass-band of the band-pass, contributes to the measurement. Using the high-pass filtering, an overdrive of the current/voltage-conversion by low-frequent interferences is avoided.

An advantageous apparatus for carrying out the method according to the present invention is subject of claim 10.

Appropriate embodiments and designs of the apparatus according to the present invention are subject of the claims 11 to 17.

Figure 2:
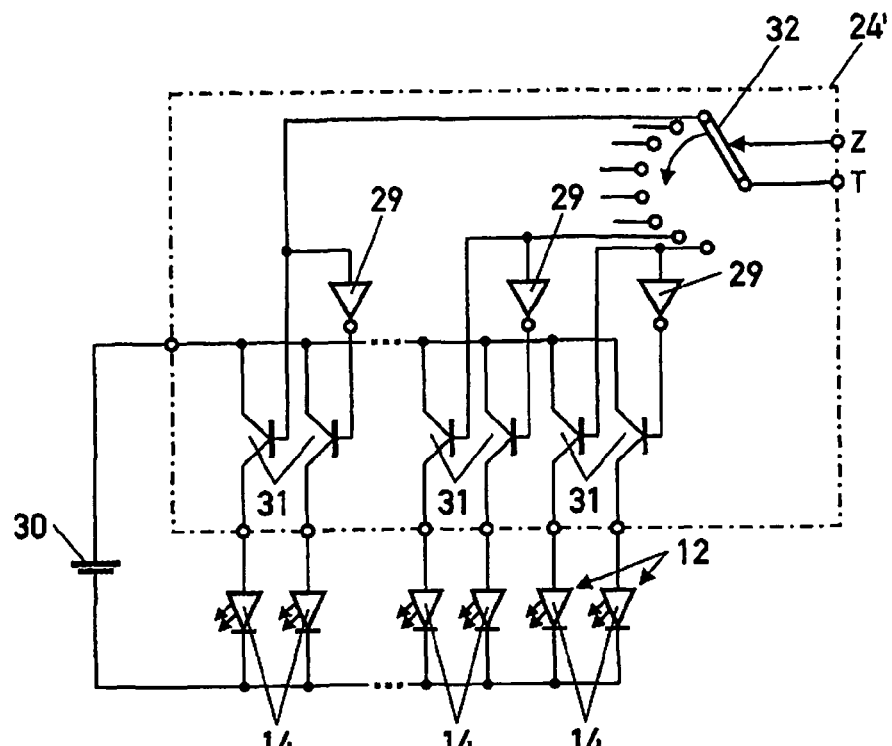
Figure 3:
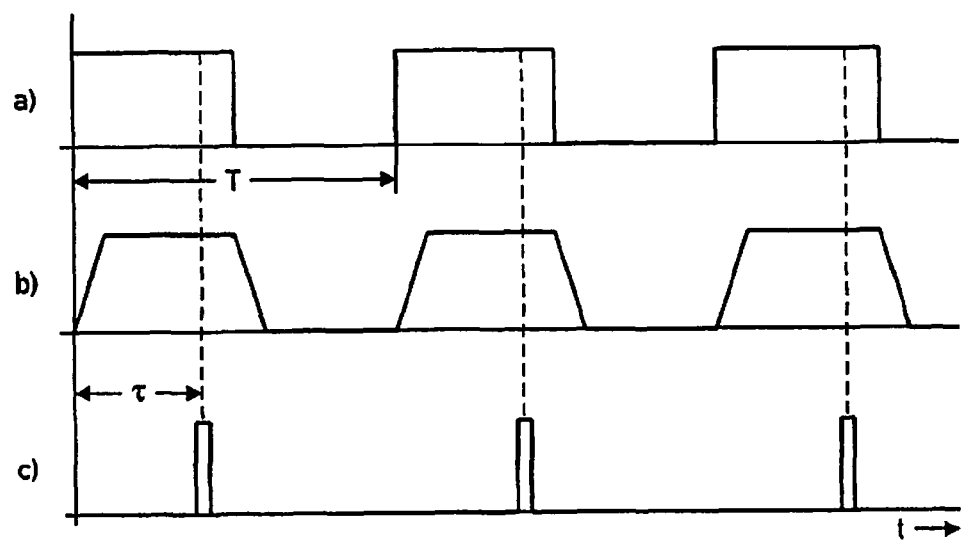

The invention is specified by an example of carrying out the invention with reference to the drawings, as follows:

FIG. 1: a block diagram of an apparatus for the quantitative real time analysis of fluorescent samples, FIG. 2: a drawing of the functional principle of a modified control unit for the control of light sources in the apparatus according to FIG. 1, FIG. 3: diagrams of the signal run at different devices of the apparatus.

In FIG. 1, the block diagram of an apparatus is shown, which can be used to perform a quantitative real time analysis of fluorescent samples. As an example, the apparatus is) used in connection with a polymerase chain reaction (PCR) for the determination of the amount of formed DNA. Hereby, a plurality of samples with DNA-molecules, which are to be copied or amplified respectively, are heated and annealed in repetitive three-stage cycles as described above, whereby a fluorescent dye binds to the double-stranded DNA and fluoresces upon excitation by extraneous light. In order to determine the number of DNA, which is copied in each cycle in a sample, the intensity of the light which is emitted by the sample is measured by the apparatus.

The apparatus provides a tray with a plurality of small containers 11, which are filled with the samples with DNA-molecules, the primers, the nucleotides and the fluorescent dyes. The tray is alternating heated and annealed within the cycles described above. An electrical light source 12 is assigned to each container 11 in the tray, being able to illuminate the sample contained in an assigned container 11 by an optical device 13, which allows to name each light source 12 as a sample-individual light source 12. At the example of a DNA analysis, the light sources are implemented as light diodes (LEDs) 14, which emit e.g. monochromatic light in the blue light spectrum with a wavelength of $\lambda=417$ nm. The optical device 13 comprises a semi-permeable beam splitter 27 which guides the light, which is emitted by the LEDS 14 to the containers 11 and deflects the fluorescence light emitted by the samples to a light collector 28. Arranged downstream to the light collector 28 is a light sensitive amplifier valve 15, a so called multiplier, preferably a channel-photomultiplier (CPM). In FIG. 1 is exemplary shown in dashed lines the radiation path of the light emitted by an LED 14 and of the light, which is emitted by the sample which is excited by the light to fluoresce, which does arrive at the light collector 28 through the optical devices 13. Arranged downstream to the amplifier valve 15, a signal processing means, which provide a current/voltage converter with integrated high-pass filter 16, a band-pass amplifier 17, and ND-converter 18, with a control input for the time selective initiation of the ND-conversion, and an averaging device 20.

A clocked pulse generator 23 generates a clocked pulse sequence with a constant frequency, e.g. 100 kHz with a duty cycle of 1:2, as shown in FIG. 3a. A duty cycle is understood to be, as usual, the ratio of the pulse period to the clocked pulse- or cycle-period. The clocked pulse sequence is applied to a control unit 24 for controlling the LEDS 14, to a pulse counter 25 with a clocked pulse input, a reset-input and a counter output, and is applied to the control input of the ND-converter 18 via a time delay member 26, which is adjusted to the delay time τ. The pulse counter 25 is used here exemplary for a timer, which outputs time pulses with a constant interval. Consecutive time pulses predetermine the interval, in which an LED 14 is controlled by the clocked pulse sequence. The pulse counter 25 realizes said interval by counting a predetermined number of clocked pulses of the clocked pulse generator 23 and outputs at its counter output the time pulse, which marks the interval upon reaching the predetermined number.

The control unit 24 according to FIG. 1 is formed such that the signal LEDs 14 control sequentially, i.e. during chronologically consecutive intervals, such that within each interval only a single light diode is controlled by the clocked pulse sequence of the clocked pulse generator 23. The respectively controlled LED 14 is periodically switched-on and switched-off within a clocked pulse cycle T of the clocked pulse sequence (FIG. 3 a), such that the switch-on- or activity phases of the LED 14 coincide with the pulse period of the clocked pulse sequence (FIG. 3 a). The clocked pulses are counted by the pulse counter 25 and the pulse counter 25 outputs at its counter output a time pulse upon reaching a predetermined number of clocked pulses, wherein said time pulse on the one hand resets the pulse counter 25 via the reset-input and on the other hand reaches the control unit 24 and initiates their control of the next LED 14 with the clocked pulse sequence of the clocked pulse generator 23. A number of clocked pulses, which lead to a time pulse of the counter pulse of the pulse counter 25, defines the interval wherein an LED 14 is controlled respectively. The interval is thus defined by two consecutive time pulses. During the interval, the LED 14 is repetitive switched-on and switched-off by the clocked pulse generator 23, whereby the sample in container 11, which is assigned to said LED 14, is illuminated and excited to emit light during the interval. The measurement of the intensity of the emission light of the sample does exclusively take place during the switch-on- or activity-phases of the LED 14 due to the design of the signal processing means.

The current-signal, which occurs at the output of the amplifier valve due to the emission of light, is converted by the current-/voltage converter with integrated high-pass filter 16 into a voltage signal. The lower cut-off frequency of the high-pass filter which is arranged upstream to the current-/voltage conversion is smaller than the pulse frequency of the clocked pulse sequence. The voltage-signal at the output of the current-/voltage converter 16 is amplified by the band-pass 17, and the analog output signal of the band-pass amplifier 17 reaches the ND-converter. The lower cut-off frequency of the band-pass amplifier 17 is equal to the lower cut-off frequency of the high-pass filter in the current/voltage converter 16 and the upper cut-off frequency of the band-pass amplifier 17 is about 5 to 10 times higher than the pulse frequency of the clocked pulse sequence.

In FIG. 3 b is shown the analog output signal of the band-pass amplifier 17. In the ND-converter 18 the output signal is sampled once according to each clocked pulse of the clocked pulse sequence and the sample value is analogue/digitally converted. In order to filter out the tuning process of the output signal, the sampling is time shifted respective to the rising slope of the clocked pulse, as it is shown in FIG. 3 c, which shows the sample values of the analog output signal. Accordingly, the clocked pulse sequence is applied to the control input of the ND-converter 18 via the time delay member 26 with its delay time τ. The delay time τ at the time delay member 26 is adjusted such that the sampling of the output signal occurs approximately in the centre of the pulse period of the clocked pulse or shifted slightly from the centre towards the end of the pulse period. Since the switch-on-or activity-phase of the LEDs 14 coincide with the pulse period, the sampling of the output signal occurs correspondingly in the centre of the switch-on phase of the LEDs 14 or shifted slightly from the centre towards the end respectively. All digital sample values which accumulate during one interval are added and the sum is averaged. This occurs in the averaging device 20 for the example of the apparatus as shown. Accordingly, the averaging device 20 usually comprises an adder and a divider, which divides the sum of the digital sample values, which accumulate within one interval, by the number of clocked pulses and thereby by the number of sample values. The averaging device 20 is reset by the time pulse of the pulse counter 25 at the end of each interval and after the output of the electrically determined value of the present light intensity, formed from the average value. This operation is repeated for each LED 14. All the obtained electrically determined values of the present light intensities of the illuminated samples are individually stored with their assignment to the respective sample and registered.

Within each of the repetitive cycles of the PCR, the above mentioned operation is repeated for each LED 14. The determined values, which are obtained in each cycle for each individual LED 14 or sample, respectively, are stored with the assignment to the cycle number and evaluated for analysing the samples.

In a method for the quantitative real time analysis which is modified compared to the above described method, the LEDs 14 are not individually and sequentially controlled, but pair-wise, i.e. during each of the consecutive intervals always a pair of LEDs 14 is controlled, such that the time of measurement is halved compared to the above described method. Hereby the control of the LED pairs is performed such that the one LED 14 is controlled by the clocked pulse sequence and the other LED 14 with the inverse clocked pulse sequence which is the clocked pulse sequence shifted by one pulse period. Accordingly, as it is shown in FIG. 2 only in principle and not as a specific example of circuitry, the one LED 14 is controlled directly and the other LED 14 is controlled via an inverter 29 by the clocked pulse sequence. At the end of the interval the next LED pair is assigned to the clocked pulse generator 23 by each time pulse of the pulse counter 25. The switch-on of the individual LEDs 14 can, as exemplarily shown in the control unit 24 in FIG. 2, which is modified compared to FIG. 1, be performed by means of electronic switches 31, which connect the direct voltage of the direct voltage source 30 to the LEDs 14 for lengths of each clock pulse. The sequential powering up of the switch pairs which are respectively assigned to an LED pair occurs e.g. via a multiplexer 32, to which the output of the clocked pulse generator 23 is connected and whose control input is connected with the counter output of the pulse counter 25. With each time pulse at the counter output of the pulse counter 25, the clocked pulse sequence is applied at the control input of the following pairs of electrical switches 31 by the multiplexer 32, namely directly at the control input of the one electrical switch 31 and, inverted by the inverter 29, at the control input of the other electrical switch 31.

Besides the exemplary described field of application relating to DNA analysis, the invention can be used for other analysis methods, at which a growth or an increase of sample contents is to be detected and evaluated quantitatively.

The invention claimed is:

1. Apparatus for the quantitative real time analysis of fluorescent samples, with a plurality of sample individual light sources (12) for the fluorescence excitation of the samples and with a light sensitive amplifier valve (15), the apparatus providing signal processing means for receiving the light emitted by the samples and for outputting electrical determined values, which are equivalent to the intensity of the light emissions, characterized in that the means comprise an A/D-converter (18) which is arranged downstream to the amplifier valve (15) and which has a control input for the time-point-wise initiation of the A/D-conversion, and provide an averaging device (20), which is arranged downstream to the A/D-converter (18), that a clocked pulse generator (23), which generates a clocked pulse sequence with constant pulse frequency and constant pulse ratio, is connected to control unit (24) for the light sources (12) and via a time delay member (26) to the control input of the A/D converter (18), that a time pulse device is provided, which generates a time pulse at its output after a predetermined number of clocked pulses and that the output of the time pulse device is connected to the control unit (24) for the light sources (12) and to the reset input of the averaging device (20).

2. Apparatus according to claim 1 wherein said signal processing means further comprises a current-/voltage converter with integrated high-pass filter (16) and one downstream band-pass amplifier (17), which are arranged between the light sensitive amplifier valve (15) and the A/D-converter (18).

3. Apparatus according to claim 2 wherein the lower cut-off frequency of the high-pass filter (16) is smaller than the pulse frequency of the clocked pulse sequence and the upper cut-off frequency of the band-pass amplifier (17) is 5 to 10 times the pulse frequency.

4. Apparatus according to claim 1 wherein the control unit (24) for the light sources (12) is formed such that each light source (12) is controlled by the clocked pulse sequence of the pulse generator (23) within an interval which is determined by the time pulses of the time pulse device and that the control is shifted with each time pulse sequentially from light source (12) to light source (12).

5. Apparatus according to claim 1 wherein the control unit (24) for the light sources (12) is formed such that during an interval, which is determined by the time pulses one light source (12) of a pair of light sources is controlled by the clocked pulse sequence and the other light source (12) of the pair of light sources is controlled by the inverted clocked pulse sequence of the pulse generator (23) and the control is shifted with each time pulse sequentially from pair of light sources to pair of light sources.

6. Apparatus according to claim 1 wherein the time pulse device is a pulse counter (25), which provides a clocked pulse input connected to the pulse generator (23), a reset input and a counter output, which is connected to the reset input and the control unit (24), and that the pulse counter (25) is formed such that it generates at its counter output a time pulse after a predetermined number of clocked pulses.

7. Apparatus according to any one of claims 1 to 6 wherein the light sources (12) are light emitting diodes (14), which preferably emit a monochromatic light with a wavelength of $\lambda \approx 417$ nm.

8. Apparatus according to claim 7 wherein the samples contain comprise DNA molecules and, bindable to them, fluorescent dyes.

9. A method for the quantitative real time analysis of fluorescent samples, at which the samples are excited to fluoresce by sample-individual light sources (12) and the intensity of the light which is emitted by the fluorescent samples is measured, characterized in that within a defined interval each light source (12) is periodically switched-on and switched-off with a clocked pulse sequence of constant pulse frequency and the measurement of the intensity of the emission light of the samples is performed exclusively during the switch-on phases of the light source (12), whereupon the emission light is converted into an electrical analog signal, which is then high-pass filtered, current/voltage converted and subsequently amplified band-limited, wherein the clocked pulse sequence is generated with a duty cycle of 1:2 and within each of said consecutive intervals one pair of light sources is controlled such that the one light source (12) of the pair of light sources is controlled by the clocked pulse sequence and the other light source (12) is controlled by the inverted clocked pulse sequence.

10. The method according to claim 9, wherein the light sources (12) are controlled individually with the clock pulse sequence in consecutive intervals.

11. The method according to claim 9, wherein the analog signal is sampled at points of time that are determined by the clocked pulse and the analog sampled value is digitized and all digital sampled values contained in one interval are added and the averaged sum of the digital sampled values is output as a measure of the light intensity.

12. The method according to claim 11, wherein the sampling of the analog signal is performed approximately in the centre of the pulse period of each clocked pulse, preferably slightly shifted from the centre towards the end of the clocked pulse period.

13. The method according to claim 12, wherein the lower cut-off frequency of the high-pass filtering is smaller than the pulse frequency of the clocked pulse sequence and the upper cut-off frequency of the band-pass amplification is set to approximately 5 to 10 times the pulse frequency.

14. The method according to claim 9, wherein the fluorescent samples comprise DNA molecules with a bindable fluorescent dye.

15. The method according to any one of claims 9 to 14, wherein light emitting diodes (14) are used as light sources, which preferably emit a monochromatic light in the blue light spectrum.

\* \* \* \* \*

UNITED STATES PATENT AND TRADEMARK OFFICE
CERTIFICATE OF CORRECTION

PATENT NO.        : 8,674,325 B2
APPLICATION NO. : 12/445267
DATED             : March 18, 2014
INVENTOR(S)       : Schliesser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1321 days.

Signed and Sealed this

Twenty-ninth Day of September, 2015

Michelle K. Lee
*Director of the United States Patent and Trademark Office*